United States Patent [19]

Siedel et al.

[11] Patent Number: 5,094,943
[45] Date of Patent: Mar. 10, 1992

[54] PROCESS AND REAGENT FOR THE IMPROVED QUANTITATIVE COLORIMETIC DETERMINATION OF HYDROGEN PEROXIDE

[75] Inventors: Joachim Siedel, Bernried; Albert Röder, Seeshaupt; Joachim Ziegenhorn, Starnberg, all of Fed. Rep. of Germany

[73] Assignee: Boehringer Mannheim GMBH, Mannheim, Fed. Rep. of Germany

[21] Appl. No.: 147,576

[22] Filed: Jan. 19, 1988

Related U.S. Application Data

[63] Continuation of Ser. No. 809,054, Dec. 12, 1985, abandoned.

[30] Foreign Application Priority Data

Dec. 20, 1984 [DE] Fed. Rep. of Germany ....... 3446637

[51] Int. Cl.$^5$ .............................................. C12Q 1/26
[52] U.S. Cl. ........................................ 435/25; 435/26; 435/28; 435/190; 435/191
[58] Field of Search ................. 435/25, 26, 28, 190, 435/191, 805

[56] References Cited

U.S. PATENT DOCUMENTS 4,454,094 6/1984 Biorling et al. ..................... 435/805

FOREIGN PATENT DOCUMENTS 59-66899 4/1984 Japan .

OTHER PUBLICATIONS

Patent Abstracts of Japan, Aug. 3, 1984, 70C236 Item #5966899.
Chem. Abstracts, vol. 102, No. 15, 15 Apr. 1985.
Yamakura (1984) Biochemical and Biophysical Research Communications, vol. 122, No. 2 (Jul. 31, 1984) pp. 635–641.

Primary Examiner—Christine Nucker
Assistant Examiner—Laurie Scheiner
Attorney, Agent, or Firm—Felfe & Lynch

[57] ABSTRACT

The present invention provides a process for the improved colorimetric determination of hydrogen peroxide as formed by a hydrogen peroxide-producing oxidase, by addition of a chromogenic system and measurement of the colored material formed, wherein superoxide dismutase (E.C. 1.15.1.1) is added to the reagent solution.

The present invention also provides a reagent for the improved colorimetric determination of hydrogen peroxide, comprising a hydrogen peroxide-producing oxidase, a chromogenic system, a buffer and optionally adjuvant enzymes, wherein it also contains superoxide dismutase.

20 Claims, 3 Drawing Sheets

Y = A+B x X
A = -.0001    B = .0462
A = -.0130    B = .0394

PROCESS AND REAGENT FOR THE IMPROVED QUANTITATIVE COLORIMETIC DETERMINATION OF HYDROGEN PEROXIDE

This application is a continuation of application Ser. No. 809,054, filed Dec. 12, 1985, now abandoned.

The present invention is concerned with a process and a reagent for the improved colorimetric determination of hydrogen peroxide.

Due to the development of simple and accurate detection processes for hydrogen peroxide in aqueous, neutral media in recent years, the use of hydrogen peroxide-producing oxidase reactions has achieved considerable importance in enzymatic analysis. This is of special interest in routine determination of various substances of high clinical-diagnostic significance in body fluids, such as blood serum and plasma or urine.

Determination of hydrogen peroxide is used frequently to determine a particular substance acted upon, e.g., by an enzyme. In a case such as this, the enzyme acts upon the substance to produce specifically a product which is in turn acted upon, e.g., by oxidase, resulting in specific production of hydrogen peroxide. The hydrogen peroxide is typically determined by electrochemical measurement processes or, most preferably, colorimetrically. Those reagents of the Trinder type have proved to be especially useful in determining formation of hydrogen peroxide because, in the presence of peroxidase (E.C. 1.11.1.7), Prinder type reagents containing phenol or phenol derivatives or substituted anilines and 4-aminoantipyrine form a red to violet coloured material, the amount or intensity of which bears a linear relationship to the amount of reacted hydrogen peroxide.

In addition, other colour indicator systems based on a similar principle have also achieved some importance. For example, instead of 4-aminoantipyrine, 3-methyl-2-benzothiazolinone hydrazone (MBTH) or its 2'-sulphonated analogue (MBTH-S) is used as coupler, preferably in combination with substituted anilines (see, for example, Clin. Chem., 17, 1154–1159/1971). However, it has been shown that these systems can only be used in reagents, which have a pH of <7; otherwise, an autoxidative colour reaction can occur even in the absence of hydrogen peroxide, resulting in a relatively rapid coloration and thus of distinctly limited storage stability of the ready for use reagent.

There are a number of advantages of such methods of analysis, for example in comparison with test processes based upon dehydrogenase reactions in which the formation or consumption of NAD(P)H is measured in the UV range. The advantages include generally much stability of the analysis reagent as well as a substantially smaller and, in some cases, even disregardable interference of the test batch due to inherent colorations or turbidities of the sample material in the visible wavelength range. There is also some flexibility (possibilities of controlling and influencing) with regard to the sensitivity of the detection reaction, depending upon the chromogenic compounds used which are suitable for the colour reaction employed.

However, this flexibility is somewhat limited. For example, with the colour indicator system peroxidase/phenol/4-aminoantipyrine, the sensitivity of detection, which is approximately comparable with that of an NAD(P)$^+$-dependent dehydrogenase reaction (cf. Methods of Enzymatic Analysis, 3rd edition, pub. Verlag Chemie, Weinheim, 1983, Vol. I, Chap.2.6.1.2), one can readily determine a relatively highly concentrated serum component, such as total cholesterol (sum of free and fatty acid-esterified cholesterol, normal concentration about 5.7 mmol/liter, one can detect reactions enabled via the coupling of cholesterol esterase (E.C. 3.1.1.13), as well as cholesterol oxidase (E.C. 1.1.3.6), which finally form hydrogen peroxide) even in the case of the use of only 20 µl. of sample per 2.0 ml. of analysis reagent, with high exactitude (measurement signal in the normal concentration range about 0.26 or 0.38 extinction units at 546 nm or $\lambda_{max}=500$ nm, respectively), while disregarding the inherent extinction of the sample.

In contradistinction thereto, for example in the In contrast, however, in carrying out, for example serum creatinine determination (detection via the successive reactions catalysed by creatininase (E.C. 3.5.2.10), creatinase (E.C. 3.5.3.3), as well as sarcosine oxidase (E.C. 1.5.3.1)) (pH optimum about 8.0), this method fails to provide precision comparable to the cholesterol test even under ideal conditions. Thus, even when using the presently most sensitive known Trinder colour indication system (2,4,6- triiodo- or 2,4,6-tribromo.3-hydroxybenzoic acid) as colour coupler with 4-aminoantipyrine.

In principle, this object could admittedly be achieved by increasing the sample/reagent ratio but, in the case of such a measure, one must be prepared for very significant disturbances of the measurement. For example, in the analysis of turbid (i.e., lipaemic or triglyceride rich) samples, or samples containing reducing components which have a negative influence on the colour reaction, such as ascorbic acid, bilirubin, as well as certain pharmaceuticals.

This also applies to other serum metabolites present in low concentrations, for example uric acid (normal value in the low concentrations 140 to 400 µmol/l.). In the case of serum uric acid determination by means of uricase (E.C. 1.7.3.3), usually one uses a maximum of 50 µl. of sample per 2.0 ml. of analysis reagent in order to be able to avoid the simultaneous determination of a sample blank value (which, in the case of serum creatinine determination, is unavoidable because of the significant amounts of creatine simultaneously present) and thus to simplify analysis procedure. Under these conditions, with the triiodo- or tribromohydroxybenzoic acid/4-aminoantipyrine colour indicator system, one obtains relatively low extinction values (about 0.045 to 0.13 at 546 nm, or 0.064 to 0.186 at 510 nm) in the measurement range.

Finally, in the case of the determination of creatinine according to the above-mentioned reaction scheme using colour indicator systems of the Trinder type (tribromo- or triiodohydroxybenzoic acid as phenolic coupling component or N-ethyl-N-$\beta$-sulpho-ethyl-m-toluidine (EST) as anilinic coupling component for 4-aminoantipyrine), it has been found that, when using aqueous creatinine standards of various concentrations, the resulting reference line does not cross the origin of the coordinate system (x axis: concentration of creatinine in the sample; y axis: colour measurement signal in extinction units) but rather has a negative y axis intercept of the order of magnitude of about 0.015 (tribromohydroxybenzoic acid/4-aminoantipyrine system, $\lambda=546$ nm) or of about 0.013 (EST/4-aminoantipyrine system, $\lambda=578$ nm) which amounts to about 20 to 33% of the normal value signal (see Examples 1 and 4) and considerably falsifies the calibration of such a test, especially when using single-point calibration.

Therefore, it is an object of the present invention to provide a process and a reagent which, on the one hand, being about a distinct increase in the sensitivity of the detection of hydrogen peroxide-producing oxidase reactions as such and, on the other hand, also prevents the appearance of axis intercepts in the case of plotting associated calibration lines and thus, overall, to improve the detection of hydrogen peroxide-producing oxidase reactions substantially.

Thus, according to the present invention, there is provided a process for the improved colorimetric determination of hydrogen peroxide, which is formed by a hydrogen peroxidase-producing oxidase, by the addition of a chromogenic system and measurement of the coloured material formed, wherein superoxide dismutase (E.C. 1.15.1.1) is added to the reagent solution.

Cu, Zn-superoxide dismutase has proven to be especially suitable within the scope of the present invention. This enzyme can be obtained from erythrocytes, for example from bovine blood. It contains 2 moles each of copper and zinc and has a molecular weight of about 33,000. However, Cu, Zn-superoxide dismutase is also present in other materials, for example in yeast.

The superoxide dismutase is preferably added in an amount of from 10 to 150 $\mu$g./ml. of reagent solution and especially preferably in an amount of from 25 to 75 $\mu$g./ml. of solution. 1 $\mu$g. of superoxide dismutase as used herein is defined as about 4U of a commercially-available superoxide dismutase preparation. This relationship is based upon the method for the determination of the activity of superoxide dismutase described in J. Biol. Chem., 244, 6049/1969.

As chromogenic systems, all chromogenic systems which react with hydrogen peroxide to form a coloured material, provided that they do not contain any components which impair the activity of the superoxide dismutase or of other enzymes present. Numerous chromogenic systems of this type are well-known and do not here require a detailed explanation. A chromogenic system of the Trinder type is preferred. This contains, as essential components, peroxidase, phenol or a phenol or aniline derivative and 4-aminoantipyrine. Especially preferred phenol derivatives for this purpose are 2,4,6-triiodo-3-hydroxybenzoic acid and the corresponding tribromo compound. Preferred aniline derivatives are N-ethyl-N-$\beta$-sulphoethyl-m-toluidine and N-ethyl-N-$\beta$-hydroxyethyl-m-toluidine. Another preferred chromogenic system consists of peroxidase, an aniline derivative and MBTH (3-methyl-2-benzothiazolinone hydrazone) or MBTH-3. In this system, as aniline derivatives, besides the two compounds already mentioned above, there can also preferably be used N,N-dimethylaniline and N,N-dimethylaminobenzoic acid.

The present invention gives especially good results when the hydrogen peroxide-producing oxidases sarcosine oxidase, uricase and oxalate oxidase are used. However, other hydrogen peroxide-producing oxidases can also be used.

This finding was not foreseeable and, at present, cannot be satisfactorily explained since it is not in accord with the known enzymatic property of superoxide dismutase, namely, the catalysis of the reaction:

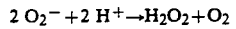

$$2 O_2^- + 2 H^+ \rightarrow H_2O_2 + O_2$$

to a significant extent which, according to a degree which, given the foregoing equation would explain additional hydrogen peroxide production and thus an improved hydrogen peroxide detection reaction, via addition of superoxide dismutase. Thus, for example, in Agric. Biol. Chem., 44, 1391/1980, it is expressly pointed out that sarcosine oxidase from *Cylindrocarpum didvmum* M-1 gives stoichiometric amounts of hydrogen peroxide in the case of the oxidation of sarcosine. The same ascertainment was also made for the sarcosine oxidase from Corynebacterium (J. Biochem., 89, 599/1981). Also in the case of the oxidation of uric acid by means of uricase, while hydrogen peroxide was formed, no superoxide radical was detected (Arch. Biochem. Biophys., 163, 359/1974).

Also, action of superoxide dismutase according to the above-given equation is contraindicated by the finding that, in the case of the replacement of the superoxide dismutase by copper complexes, which display outstanding effectiveness with respect to $O_2^-$ disproportionation which, in some cases, even exceeds that of superoxide dismutase, such as Cu(acetylsalicylate)$_2$, Cu(lysine)$_2$ or Cu$_2$(indomethacine)$_4$ (cf. Bull. europ. Physiopath. resp., 17 (suppl.), 73/1981). Even when concentrations of the oxidase reagent of up to 100 $\mu$mol/l. are used (the highest superoxide dismutase concentration used in the following Examples only amounts to 3.8 $\mu$mol/l), no improvement of hydrogen peroxide detection is brought about.

Furthermore, the action of the superoxide dismutase with regard to the axis intercept removal is not explicable on the basis of the above-given reaction equation since, even if a certain $O_2^-$ were formed by the mentioned oxidases present, contrary to the statements in the literature, this would, in the case of substrate conversion tending towards zero, also have to tend towards zero.

Finally, the effect of the superoxide dismutase addition improving the detection of hydrogen peroxide-producing oxidase reactions is equally marked in phosphate-free reagents (buffered, for example, by TES, 100 mmol/l.) as well as in solutions buffered with phosphate (concentration in the reagent 100 to 150 mmol/l.) although the literature states that the enzymatic activity for the especially preferred superoxide dimutase, i.e., that obtained from bovine erythrocytes, is strongly inhibited by phosphate. The reference Biochemistry 23:2079 (1984) states that the superoxide dimutase is inhibited by about 50% at a phosphate concentration of only 10 mmol/l.

The present invention also provides a reagent for the improved colorimetric determination of hydrogen peroxide, comprising a hydrogen peroxide-producing oxidase, a chromogenic system, buffer and possibly auxiliary enzymes, wherein it contains superoxide dismutase.

The statements made above with regard to the process also apply to the composition of the reagent. For the analysis of serum components, it is preferable to add a clarification system to the reagent according to the present invention, for example in the form of a mixture of a non-ionic tenside with salts of bile acids, such as sodium cholate, as well as a lipase (E.C.3.1.1.3) in order also to be able to measure lipaemic samples without disturbance by background turbidities. Finally, the reagent according to the present invention can preferably also contain a preserving agent, such as sodium azide, agents for the removal of disturbances of the hydrogen peroxide detection reaction brought about by ascorbic acid and/or bilirubin present in the samples, such as ascorbate oxidase and potassium ferrocyanide, as well as small amounts of heavy metal complex formers, such as ethylenediamine-tetraacetic acid (EDTA). The amounts or concentrations of these substances and the components of the chromogenic system and of the buffer correspond to those of the known reagents and, therefore, do not require further explanation.

The reagent according to the present invention can also be present on a solid, inert, optionally multi-layer carrier material, for example it can be impregnated into test strips, and thus permit so-called dry chemical analyses.

By means of the additive used according to the present invention, the sensitivity of the hydrogen peroxide detection can =increased by about 22 to 34%, especially in the case of the preferred colour-producing systems of the Trinder type (depending upon the nature of the oxidase reaction used, as well as upon the composition of the associated analytical reagent) and, at the same time, the appearance of axis intercepts in the production of calibration lines (not only in the case of indicator systems of the Trinder type but also in the case of systems with MBTH or MBTH-S, as well as aniline derivatives as colour coupling components) can be avoided or at least reduced to an extent which, from the analysis point of view, is neglegible.

The following Examples are given for the purpose of illustrating the present invention, reference thereby being made to the accompanying drawings, in which.

EXAMPLE 1

Improvement of the detection of hydrogen peroxide in the completely enzymatic determination of creatinine a) Colour reagent

| TES.KOH (pH 7.9) | 100 mmol/l |
| --- | --- |
| sodium chloride | 150 mmol/l. |
| 4-aminoantipyrine | 0.75 mmol/l. |
| 2,4,6-tribromo-3-hydroxy-benzoic acid | 8.6 mmol/l. |
| potassium ferrocyanide | 10 μmol/l. |
| EDTA | 50 μmol/l. |
| creatininase E.C. 3.5.2,10 | 20 U/l. |
| creatinase E.C. 3.5.3.3 | 10 U/l. |
| sarcosine oxidase E.C. 1.5.3.1 | 6.5 U/ml. |
| peroxidase E.C. 1.11.1.7 | 2 U/ml. |
| superoxide dismutase | 0–150 μg./ml. |
| | ( 0–600 U/ml.) | b) Test batch: T=25° C.; λ=546 nm; d=1.0 cm.

| | sample value (P) | reagent blank (L) |
| --- | --- | --- |
| colour reagent | 2.00 ml. | 2.00 ml. |
| sample[+)] | 0.10 ml. | — |
| distilled water | — | 0.10 ml. | incubate for 20 minutes, then measure extinction of

-continued

| | sample value (P) | reagent blank (L) |
| --- | --- | --- |
| P against L. $\Delta A = A_P - A_L$ | | |

[+)]As sample material, there was used Preciset ® creatinine (Boehringer Mannheim GmbH. Cat. No. 125 547). For the determination, independent of possible axis intercepts, of the extinction difference achieved with 1 mg./dl. creatinine concentration in the sample, all standards were used as sample (1 to 6 mg./dl.) and the slope of the correlation lines ΔA/(y axis) against creatinine, mg./dl. (x axis) used as a measure for ΔA/mg./dl. creatinine.

Figure 1:
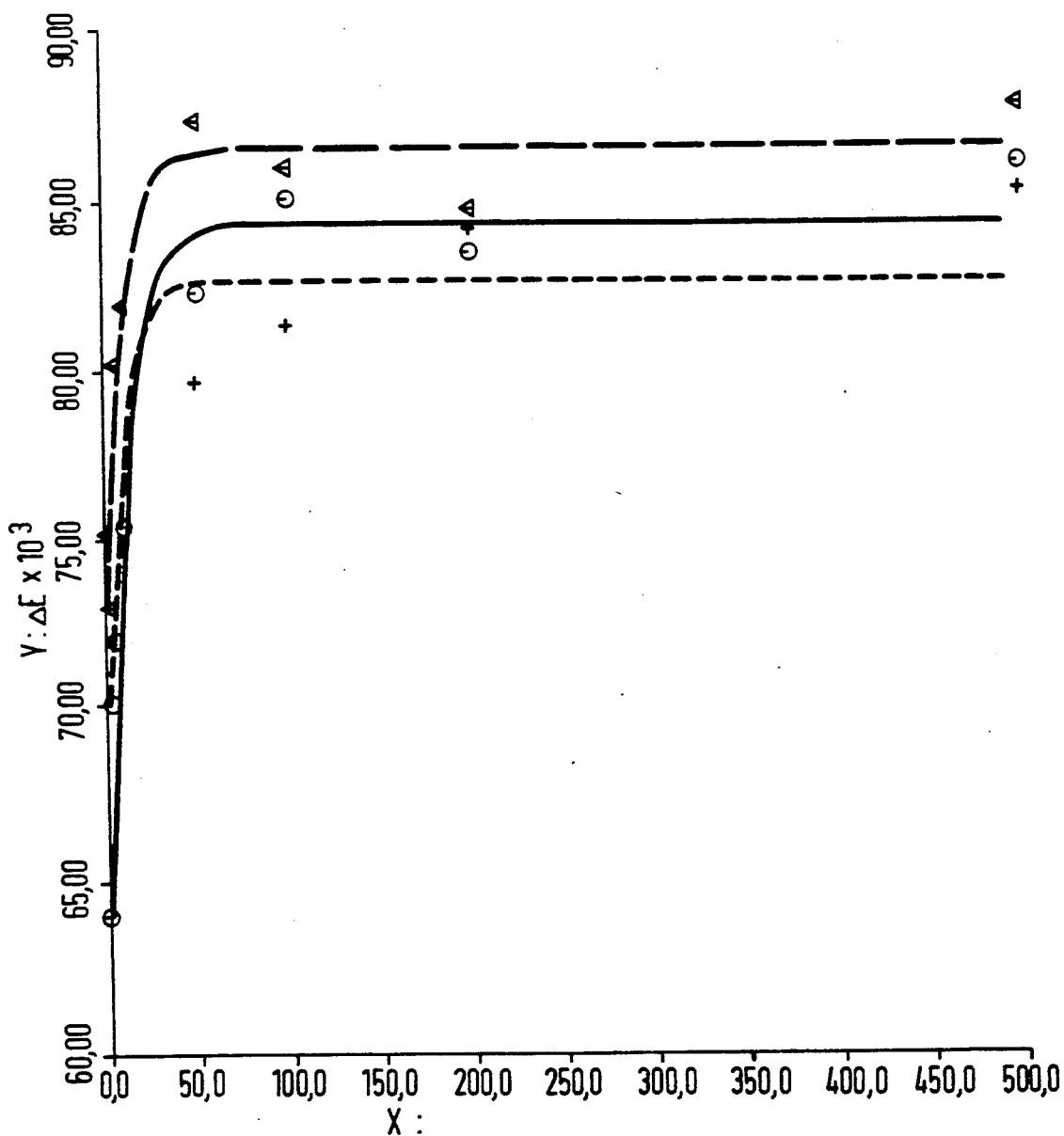
FIG. 1 is a graphic representation in which the superoxide dismutase (SOD) activity is plotted against the $H_2O_2$-detection sensitivity for Examples 1 to 3.

The dependence of the reference line slope upon the superoxide dismutase activity present in the colour reagent (0, 2, 5, 10, 50, 100, 200 and 500 U/ml.) is shown in FIG. 1 of the accompanying drawings (unbroken line). As can be seen, in comparison with the reagent without superoxide dismutase, when about 50 μ/ml or more of superoxide dismutase was added to the reagent, a plateau with an approximately 31% increase, of sensitivity of the hydrogen peroxide detection is achieved; an increase of the superoxide dismutase concentration above 150 μg./ml. is certainly readily possible but gives no improvement with regard to the maximum achievable sensitivity increase and is, therefore, for economic reasons, not preferred. The negative y axis intercept (reference line) with the reagent without superoxide dismutase amounted to 0.015 extinction units, whereas in the case of the reagents with superoxide dismutase activities of 50 to 500 U/ml. it only amounted to 0.002 extinction units.

The results do not change when, instead of 2,4,6-tribomo-3-hydroxybenzoic acid, the analogous triiodo compound as colour coupler is used.

If, in the above-mentioned colour reagent, creatininase alone or creatininase and creatinase are omitted, then the determination of creatine or sarcosine is also possible without the effect according to the present invention of the superoxide dismutase being lost.

EXAMPLE 2

Improvement of the Detection of Hydrogen Peroxide in the Enzymatic Determination of Creatinine a) Colour reagent: as reagent a) of Example 1. Additionally, as clarification agent, there were added thereto 0.25% n-decanol polyglycol ether (Lutensol ®ON 50), 5 mmol/l. sodium cholate, as well as 2 U/ml. lipase (from *Candida cylindracea*).

b) Test batch: Test batch and evaluation of the measurement took place according to Example 1,b). The measurement results are reproduced in FIG. 1 of the accompanying drawings (dashed line with triangles as measurement points).

EXAMPLE 3

Improvement of the Detection of Hydrogen Peroxide in the Enzymatic Determination of Creatinine a) Colour reagent: as reagent a) of Example 2. Instead of the TES buffer, there was used potassium phosphate buffer (pH 7.8), 150 mmol/l. and the addition of sodium chloride was omitted.

b) Test batch: test batch and evaluation of the measurement took place according to Example 1, b). The results of the measurement are reproduced in FIG. 1 of the accompanying drawings (dashed lines with crosses as measurement points).

EXAMPLE 4

Figure 2:
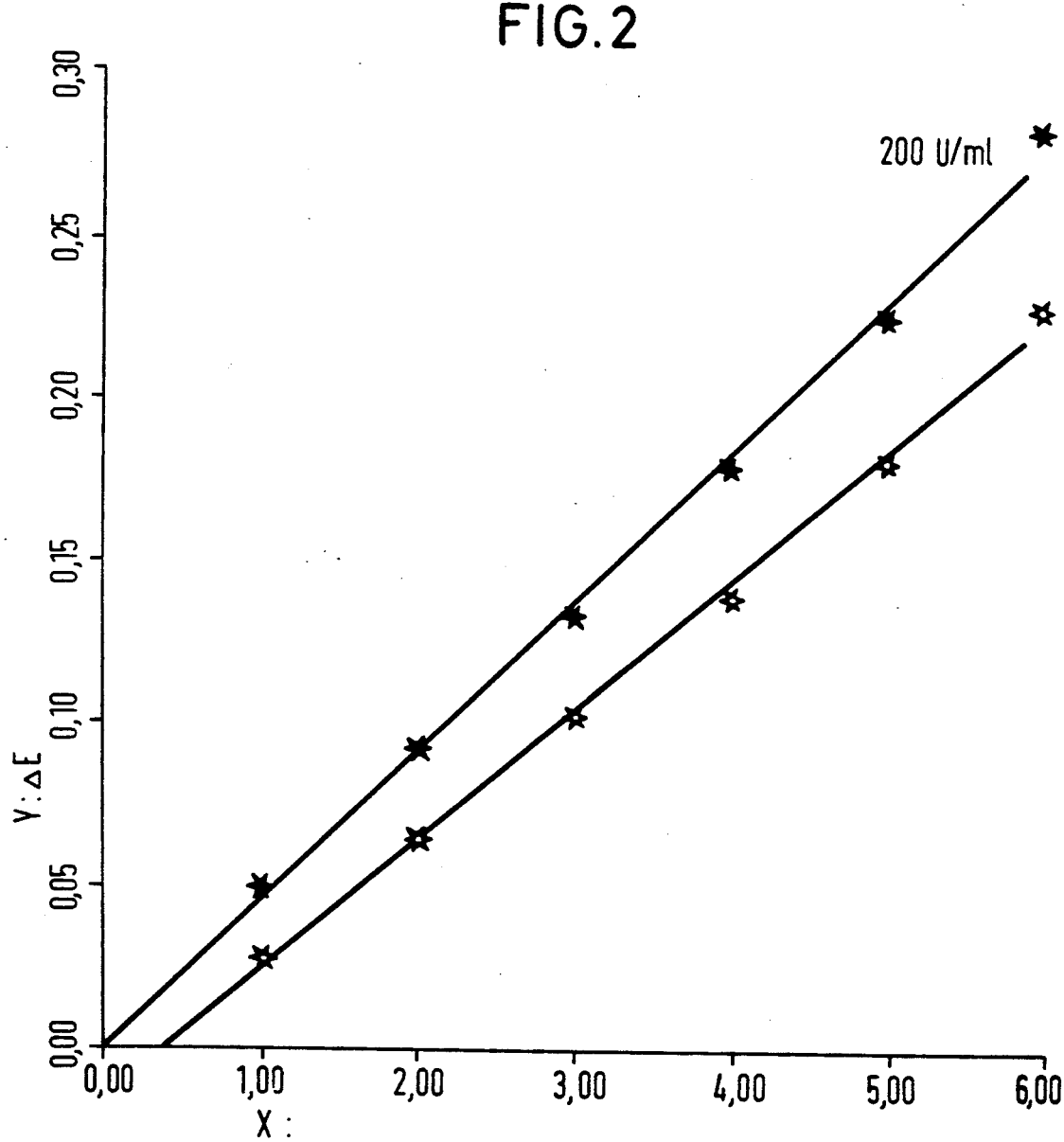
FIG. 2 is a graphic representation of the reference curves according to Example 4.

Improvement of the Detection of Hydrogen Peroxide in the Enzymatic Determination of Creatinine a) Colour reagent: as reagent a) from Example 3. However, instead of triboromohydroxybenzoic acid, as colour coupler for the 4-aminoantipyrine there was used N-ethyl-N-$\beta$-sulphoethyl-m-toluidine. The superoxide dismutase activity in the reagents was 0 or 200 U/ml.

b) Test batch: took place according to Example 1, b) except that measurement was made at 578 nm and not at 546 nm. The results (reference curves) are reproduced in FIG. 2 of the accompanying drawings. The sensitivity of this colour indicator system is admittedly lower than that of the systems of Examples 1 to 3 but it can can be seen here as well that the addition of superoxide dismutase not only brings about a distinct increase of the sensitivity of the detection of the hydrogen peroxide detection (about 17.3%) but also brings about practically the complete disappearance of the y axis intercept of the correlation lines (-0.013 extinction units) measured with the reagent without the addition of superoxide dismutase.

EXAMPLE 5

Improvement of the Detection of Hydrogen Peroxide in the Enzymatic Determination of Uric Acid a) Colour reagent

| | |
|---|---|
| potassium phosphate (pH 8.0) | 100 mmol/l. |
| 2,4,6-tribromo-3-hydroxybenzoic acid | 7.5 mmol/l. |
| 4-aminoantipyrine | 0.2 mmol/l. |
| potassium ferrocyanide | 50 $\mu$mol/l. |
| EDTA | 1 mmol/l. |
| n-decanol polyglycol ether (Lutensol ® ON 50) | 5 g./l. |
| sodium cholate | 7 mmol/l. |
| uricase E.C. 1.7.3.3 | 1 U/ml. |
| peroxidase E.C. 1.11.1.7 | 3 U/ml. |
| lipase (from *C. cylindraces*) E.C. 3.1.1.3 | 2 U/l. |
| superoxide dismutase | 0 to 500 U/ml. |

Test batch: T=25° C.; $\lambda$=546 nm; d=1.0 cm.

| | sample value (P) | reagent blank (L) |
|---|---|---|
| colour reagent | 2.00 ml. | 2.00 ml. |
| sample+) | 0.05 ml. | — |
| distilled water | — | 0.05 ml. |
| incubate for 10 minutes then measure extinctions of P against L. $\Delta A = A_P - A_L$ | | |

+)As sample material, there was used Preciset ® uric acid (Boehringer Mannheim GmbH, Cat. No. 125 628). For the determination of the extinction changes achieved with 1 mg./dl. of uric acid, analogously to Examples 1 to 3, a reference curve was plotted with different uric acid standards (2 to 12 mg./dl.) and the slope thereof used as a measure for $\Delta A$/1 mg./dl. uric acid.

Figure 3:
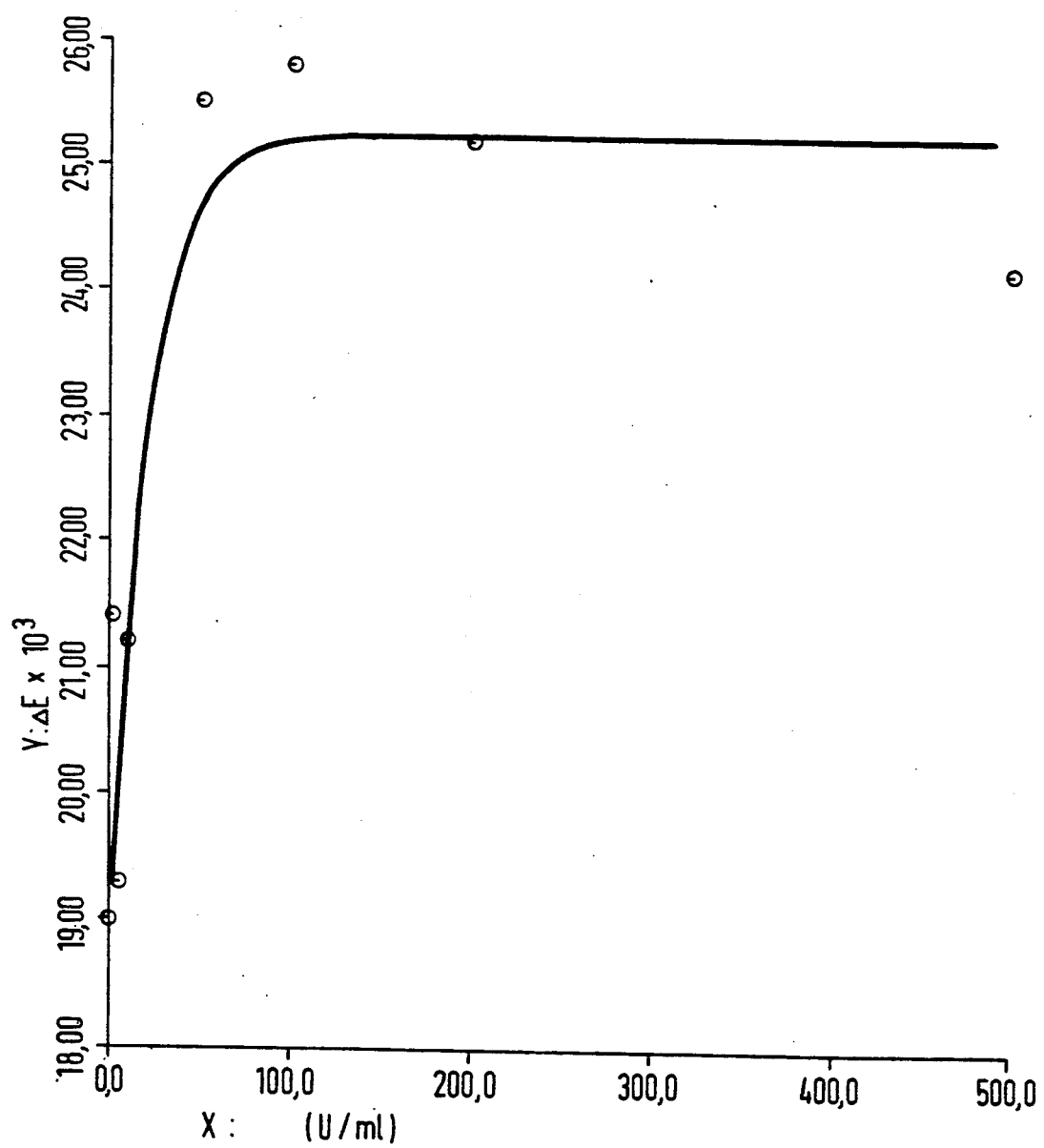
FIG. 3 is a graphic representation analogous to FIG. 1 for Example 5.

The dependence of this increase ($\Delta A$/1 mg./dl. uric acid) upon the amount of superoxide dismutase added to the colour reagent (0, 2, 5, 10, 50, 100, 200 and 500 U/ml.) is shown in FIG. 3 of the accompanying drawings.

As also in Examples 1 to 4, the tribromohydroxybenzoic acid used in the uric acid colour reagent can be replaced by the analogous triiodo compound or an aniline derivative, such as N-ethyl-N-$\beta$-sulphoethyl-m-toluidine, as colour coupler for the 4-aminoantipyrine without the improvement of the detection of the hydrogen peroxide due to the addition of superoxide dismutase being lost.

EXAMPLE 6

Improvement of the Detection of Hydrogen Peroxide in the Enzymatic Determination of Oxalic Acid with the Help of Oxalate Oxidase (E.C. 1,2,3,4), as well as of the Combination Peroxidase/MBTH-S/N,N-Dimethylaniline as Colour Indicator System a) Reagents
1. succinic acid buffer (0.5 mmol/l.; pH=3.8): 6.75 g. disodium succinate hexahydrate dissolved in 400 ml. distilled water, adjusted with 2N hydrochloric acid to pH 3.8 (25° C.) and made up to 500 ml.
2. MBTH-S
3. N,N-dimethylaniline (0.21 mol/l.); 100 $\mu$l. dimethylaniline dissolved in 3.9 ml. 0.5 N hydrochloric acid
4. oxalate oxidase: 3.33 mg. of an enzyme with 0.3 U/mg. dissolved in 1 ml. distilled water.
5. superoxide dismutase from bovine erythrocytes (pure enzyme): 12.5 mg. dissolved in 1 ml. distilled water and dilutions of 0.125, 0.250, 2.50 as well as 5.00 mg. of enzyme per 1 ml. of distilled water produced therefrom.
6. oxalate solutions: oxalic acid dissolved in water at concentrations of 1, 2, 3, 4, 5 and 6 mg./dl. (referred to 100% free acid).

b) Basic colour reagent

In 100 ml. succinic acid buffer a), 1., dissolve 2.3 mg. MBTH-S, then add thereto 40 $\mu$l. dimethylaniline solution a), 3. and mix well. To 10 ml. amounts of this mixture add either 0.10 ml water or 0.10 ml. of the peroxide dismutase solution a), 5. (end concentration 1.25, 2.50, 25.0, 50.0 and 125.0 $\mu$g. of superoxide dismutase/ml. basic reagent) and mix.

c) Test batch: T=37° C.; $\lambda$=578 nm.; d=1.0 cm.

| | sample value (P) | reagent blank (RL)+) |
|---|---|---|
| basic colour reagent | 1.00 ml. | 1.00 ml. |
| peroxidase solution | 0.01 ml. | 0.01 ml. |
| oxalate oxidase solution | 0.10 ml. | 0.10 ml. |
| sample (oxalic acid solutions) | 0.10 ml. | — |
| water | — | 0.10 ml. |
| incubate for 20 minutes then measure extinctions of P against RL. $\Delta A = \Delta A_P - \Delta A_{RL}$ | | |

+)Only one reagent blank needs to be carried out for each series of measurements.

The evaluation of the calibration curves achieved with the basic colour reagent made up with different amounts of superoxide dismutase showed a clearly positive influence of the superoxide dismutase in the overcoming of the y axis intercept (y, extinction units; x, oxalic acid sample concentrations):

TABLE I y axis intercept of the calibration lines determined with the oxalic acid samples of different concentrations in the case of differing superoxide dismutase concentrations in the basic reagent:

| superoxide dismutase concentration in the basic colour reagent ($\mu$mg./ml.) | 0.00 | 1.25 | 2.50 | 25.0 | 50.0 | 125.0 |
|---|---|---|---|---|---|---|
| y axis intercepts of the correlation lines | −29 | −13 | −12 | −5 | −1 | 0 |

TABLE I-continued y axis intercept of the calibration lines determined
with the oxalic acid samples of different concentrations
in the case of differing superoxide dismutase concentrations in the basic reagent:

(mA)

We claim:

1. A process for colorimetric determination of hydrogen peroxide formed by a hydrogen peroxide producing oxidase which does not produce superoxide comprising adding to a non-superoxide containing sample containing said hydrogen peroxide producing oxidase a chromogenic system and superoxide dismutase in an amount sufficient to increase sensitivity of colorimetric determination of said chromatogenic system.

2. Process according to claim 1, wherein 10 to 150 μg. of superoxide dismutase/ml. of reagent solution are added.

3. Process according to claim 2, wherein 25 to 75 μg. of superoxide dismutase/ml. of reagent solution are added.

4. Process according to claim 1, wherein the superoxide dismutase is Cu, Zn-superoxide dismutase.

5. Process according to claim 1, wherein the chromogenic system is a Trinder reagent, said reagent containing 4-aminoantipyrine, peroxidase, and one member of the group consisting of phenol a phenol derivative or an aniline derivative, wherein said phenol, phenol derivative and aniline derivative oxidatively couple to 4-aminoantipyrine in the presence of $H_2O_2$.

6. Process according to claim 5, wherein, as phenol derivative, there is used 2,4,6-triiodo-3-hydroxybenzoic acid or the analogous tribromo compound.

7. Process according to claim 5, wherein, as aniline derivative, there is used N-ethyl-N-β-sulphoethyl-m-toluidine or N-ethyl-N-β-hydroxyethyl-m-toluidine.

8. Process according to claim 1, wherein the chromogenic system comprises peroxidase, an aniline derivative which oxidatively couples to 4-amino-antipyrine in the presence of $H_2O_2$ and 3-methyl-2-benzo-thiazolinone hydrazone (MBTH) or 3-methyl-2-benzo(2'-sulfo)-thiazolinone hydrazone (MBTH-S).

9. Process according to claim 8, wherein, as aniline derivative, there is used N,N-dimethylaniline, N,N-dimethylaminobenzoic acid, N-ethyl-N-β-sulphoethyl-m-toluidine or N-ethyl-N-β-hydroxyethyl-m-toluidine.

10. Process according to claim 1, wherein the hydrogen peroxide-producing oxidase is sarcosine oxidase, uricase or oxalate oxidase.

11. A reagent for colorimetric determination of hydrogen peroxide comprising a hydrogen peroxide-producing oxidase, a chromogenic system, a buffer optionally adjuvant enzymes, and superoxide dismutase in an amount effective to improve the sensitivity of the colorimetric determination of the chromogenic system.

12. Reagent according to claim 11, wherein the superoxide dismutase is Cu, Zn-superoxide dismutase.

13. Reagent according to claim 11 wherein the chromogenic system is a Trinder reagent said reagent containing peroxidase, 4-aminoantipyrine and at least one member of the group consisting of phenol a phenol derivative and an aniline derivative wherein said phenol, phenol derivative or aniline derivative oxidatively couple to 4-aminoantipyrine in the presence of $H_2O_2$.

14. Reagent according to claim 13, wherein, as phenol derivative, it contains 2,4,6-triiodo-3-hydroxybenzoic acid or the analogous tribromo compound.

15. Reagent according to claim 13, wherein, as aniline derivative, it contains N-ethyl-N-β-sulphoethyl-m-toluidine or N-ethyl-N-β-hydroxyethyl-m-toluidine.

16. Reagent according to claim 11, wherein the chromogenic system contains peroxidase, an aniline derivative which oxidatively couples to 4-amino-antipyrine in the presence of $H_2O_2$ and 3-methyl-2-benzo-thiazolinone hydrazone (MBTH) or 3-methyl-2-benzo(2'-sulfo)-thiazolinone (MBTH-S).

17. Reagent according to claim 16, wherein the aniline derivative is N,N-dimethylaniline, N,Ndimethylaminobenzoic acid, N-ethyl-N-β-sulphoethyl-m-toluidine or N-ethyl-N-hydroxyethyl-m-toluidine.

18. Reagent according to claim 11, wherein the hydrogen peroxide-producing oxidase contains sarcosine oxidase, uricase or oxalate oxidase.

19. Reagent according to claim 12, wherein said reagent contains 10 to 150 ug. superoxide dismutase per ml.

20. Reagent according to claim 11 wherein said reagent is present on a solid, inert single or multi-layer carrier material.

* * * * *

UNITED STATES PATENT AND TRADEMARK OFFICE
CERTIFICATE OF CORRECTION

PATENT NO. : 5,094,943
DATED : March 10, 1992
INVENTOR(S) : Joachim Siedel et al It is certified that error appears in the above-indentified patent and that said Letters Patent is hereby corrected as shown below:

Column 3, line 51: change "MBTH-3" to -- MBTH-S --.

Column 5, line 15: change "can=" to -- can be --;
line 59" before "O" add --  --.

Col. 10, claim 19, line 1, change "12" to --11--.

Signed and Sealed this

Fifth Day of October, 1993

*Attest:*

BRUCE LEHMAN

*Attesting Officer*   *Commissioner of Patents and Trademarks*